United States Patent
Farr

(10) Patent No.: US 11,806,653 B2
(45) Date of Patent: Nov. 7, 2023

(54) EXTRACTION ARM WITH FILTER

(71) Applicant: TBH GMBH, Straubenhardt (DE)

(72) Inventor: Fabian Farr, Remchingen (DE)

(73) Assignee: TBH GMBH, Straubenhardt (DE)

( * ) Notice: Subject to any disclaimer, the term of this patent is extended or adjusted under 35 U.S.C. 154(b) by 249 days.

(21) Appl. No.: 17/376,258

(22) Filed: Jul. 15, 2021

(65) Prior Publication Data

US 2022/0016557 A1   Jan. 20, 2022

(30) Foreign Application Priority Data

Jul. 17, 2020   (DE) ..................... 20 2020 104 146.0

(51) Int. Cl.
*B01D 46/00* (2022.01)
*B08B 15/04* (2006.01)
*A61M 1/00* (2006.01)

(52) U.S. Cl.
CPC ......... *B01D 46/0004* (2013.01); *A61M 1/784* (2021.05); *A61M 1/84* (2021.05); *B01D 46/001* (2013.01); *B08B 15/04* (2013.01); *B01D 2265/027* (2013.01); *B01D 2265/028* (2013.01); *B01D 2279/51* (2013.01)

(58) Field of Classification Search
None
See application file for complete search history.

(56) References Cited

U.S. PATENT DOCUMENTS

| 5,597,385 A | 1/1997 | Moerke |
| 6,406,454 B1 | 6/2002 | Tajianpour |
| 2018/0001241 A1* | 1/2018 | Zhibin ................. B01D 35/153 |
| 2018/0133084 A1* | 5/2018 | Kirschman ............... F24F 3/00 |

FOREIGN PATENT DOCUMENTS

| CN | 104606728 A | * | 5/2015 | ............. A61H 15/02 |
| EP | 3 679 913 A1 | | 7/2020 | |
| EP | 3679913 A1 | * | 7/2020 | ........... A61H 9/0057 |

OTHER PUBLICATIONS

CN104606728A—preview (InnovationQ Plus machine translation of Zhang) (Year: 2015).*

* cited by examiner

*Primary Examiner* — Gabriel E Gitman
(74) *Attorney, Agent, or Firm* — Oliff PLC

(57) ABSTRACT

An extraction arm for an extraction device includes a suction pipe and a suction head and defines a suction path that extends from an extraction region in the surroundings of the suction head through the suction pipe to the extraction device. The extraction arm includes an exchangeable filter which is arranged within the suction path. The filter is located in a filter housing which has a main body and a closable cover. The filter is exchangeable, which makes it very easy to prepare the extraction arm for a new application. Since the filter is arranged in front of the suction pipe, the suction pipe remains clean. The filter can easily be changed, whereby disinfection or cleaning of the suction pipe is not necessary.

7 Claims, 3 Drawing Sheets

EXTRACTION ARM WITH FILTER

The present invention relates to an extraction arm for an extraction device and to a use of the extraction arm with a medical extraction device.

Various pollutants can be released by processes in the work area. These released pollutants pose a health risk. In particular, when mixed with gases, both liquids and solids in the form of aerosols can be produced as airborne suspended particles. These aerosols are known, inter alia, as vapor, mist, or smoke. Dust particles, in particular fine dust, can include suspended matter of which the settling times are several hours.

It is known to remove such pollutants from the work area by means of an extraction apparatus. A suction arm with an extraction pipe can be used here. The extraction pipe can have a plurality of joints, so that a collecting device located at the open end of the extraction pipe, for example a suction screen, a suction nozzle or an extraction hood, can be positioned at the work area. There are also simpler designs without joints.

In the known extraction apparatuses, a filter system is usually provided, which is located in the extraction device. Extracted air containing pollutants is then fed to the extraction device by means of the suction pipe and filtered there. The disadvantage of this is that the extraction pipe is exposed to pollutants, particularly in its inner region, and thus becomes soiled.

In the case of bioactive pollutants such as viruses or bacteria, it may be necessary to clean or disinfect the extraction pipe from time to time in order to rule out a health risk due to the deposited pollutants.

The object of the present invention is therefore to produce an improved extraction arm for an extraction device, in particular for use with a medical extraction device.

In a first aspect, the invention relates to an extraction arm for an extraction device having a suction pipe and a suction head, the extraction arm defining a suction path that extends from an extraction region in the surroundings of the suction head through the suction pipe to the extraction device, and the extraction arm comprising an exchangeable filter which is arranged within the suction path.

In a second aspect, the invention relates to the use of an extraction arm, as described in the preceding paragraph, with a medical extraction device.

Preferred embodiments of the invention are described in the dependent claims. It goes without saying that the features mentioned above and those yet to be explained below can be used not only in the combination specified in each case, but also in other combinations or in isolation, without departing from the scope of the present invention.

A high extraction capacity can be achieved by means of a suction pipe, since the suction pipe is substantially robust against the effect of a negative pressure that occurs during suction. By means of a filter which, according to the invention, is arranged within the suction path, the suction path can be kept free of pollutants at least in portions. The exchangeable filter makes it possible to prepare the extraction arm for a new application with only short maintenance breaks. In particular, the intervals for cleaning and/or disinfecting the suction pipe can be extended. It is even possible that disinfection and/or cleaning of the suction pipe can be completely dispensed with by using the exchangeable filter in the suction path. In the medical field, simply changing the filter can increase the confidence of the patient and the attending doctor in the extraction device, especially if the filter change takes place in front of the patient.

In an advantageous embodiment, the filter is accommodated in a filter housing, the filter housing being designed to connect the filter and the suction pipe in an airtight manner. The use of a filter housing makes it easier to replace the filter. Furthermore, a correct arrangement of the filter within the suction path can be achieved in a technically simple manner. The design of the filter housing in such a way that the filter and the suction pipe are connected in an airtight manner allows the filter performance of the replaceable filter to be increased in a technically simple manner. The filter housing can have rubber seals. The replaceable filter can thus be produced very simply and inexpensively, since all means for producing airtightness are arranged on the filter housing.

The filter housing advantageously has a main body which is connected to the suction pipe and a removable cover for closing the filter housing. The removable cover makes it possible to change the replaceable filter quickly and easily. The main body connected to the suction pipe allows an airtight connection between the filter housing and the suction pipe in a technically simple manner. In particular, the main body can be firmly connected to the suction pipe, for example glued or welded on. Furthermore, the suction pipe can also be overmolded during the manufacture of the main body if the main body is produced in an injection molding process.

The main body particularly preferably has a connecting piece for connection to the suction pipe. The connecting piece can preferably be formed in one piece with the main body. This allows the main body and connecting piece to be manufactured inexpensively as a single injection-molded part. Such a one-piece design of the suction pipe and the main body of the filter housing is, on the one hand, mechanically very stable and, on the other hand, ensures absolute airtightness. Furthermore, a connecting piece, which is preferably arranged around the circumference of the suction pipe, allows an airtight connection between the main body and the suction pipe without reducing the effective cross-section of the suction pipe.

The filter housing advantageously has a holding means for holding the cover in a closed position. By means of a cover having a holding means, the filter housing can be closed in a technically simple manner and held in the closed position. The filter can be accommodated in a protected manner in the filter housing. In particular, this can counteract unwanted opening of the cover and slipping of the filter.

The cover particularly preferably has an air inlet, preferably in the form of a grille, in order to guide the extracted air into the interior of the filter housing. The air flow of the extracted air can be guided by means of an air inlet in the cover. An air inlet in the form of a grille allows technically simple and inexpensive production of the cover. In this way, a preferred compromise between stability and air permeability of the cover can be achieved.

In a further advantageous embodiment, the cover of the filter housing is accessible from the extraction region in order to replace the filter without using tools. This allows the filter to be exchanged quickly and efficiently. In particular, only one component, i.e. the cover of the filter housing, has to be touched and opened to replace the filter. The extraction arm is easy to use.

The suction head preferably comprises an extraction hood, in the center of which the filter housing is located. Such an extraction hood allows the extraction region to be modified. By arranging the filter housing in the center of the extraction hood, an efficient suction effect can be achieved, while at the same time providing good accessibility of the filter housing, in particular for replacing the filter. In particular, due to this advantageous arrangement, the entire extraction arm can be kept free of pollutants, since only air filtered through the filter enters the suction pipe.

The extraction hood is particularly preferably connected to the main body. It goes without saying that a one-piece connection can be provided, i.e. that the main body is formed in one piece with the extraction hood. For example, the main body can be a single injection-molded part together with the extraction hood. It also goes without saying that the extraction hood can also be connected to the main body by means of gluing, screws or other known types of connection. In particular, a detachable connection can be provided here in order to combine different extraction hoods with the same main body.

The cover of the filter housing particularly preferably has a latching means, in particular two latching means, by means of which it is releasably attached to the main body. A secure fit of the cover on the main body can be ensured by means of such a latching means. In particular, it is conceivable that the latching means presses the cover onto the main body under force, so that a secure and firm connection between the main body and the cover is achieved.

The latching means particularly preferably has a spring element which extends through a recess in the extraction hood in order to latch with the main body. A simple, secure arrangement of the cover on the main body is possible by means of such a spring element or two spring elements. The recesses on the extraction hood make it possible to loosen the spring element by hand outside of the extraction region. This reduces the likelihood of contamination when the spring element is loosened. The recesses on the extraction hood make it possible to use the same extraction hub for extraction arms with and without a filter housing. The extraction hood can consequently be manufactured inexpensively in large numbers.

The extraction region is to be understood as the region on which an extraction effect is exerted by the extraction device. It goes without saying that the extraction region is dependent on the relevant pollutant and dependent on the relevant collecting device, such as a suction nozzle, a suction screen, or a suction bell. In particular, the extraction region can be understood as a region in which a predefined percentage of a certain pollutant is removed from the air.

In the present case, a suction pipe is to be understood as a pipe that creates a connection between the suction head and the extraction device, the suction pipe guiding a suction effect of the extraction device to the extraction region.

An embodiment of the invention is described and explained in more detail below in connection with the accompanying drawings, in which.

Figure 1:
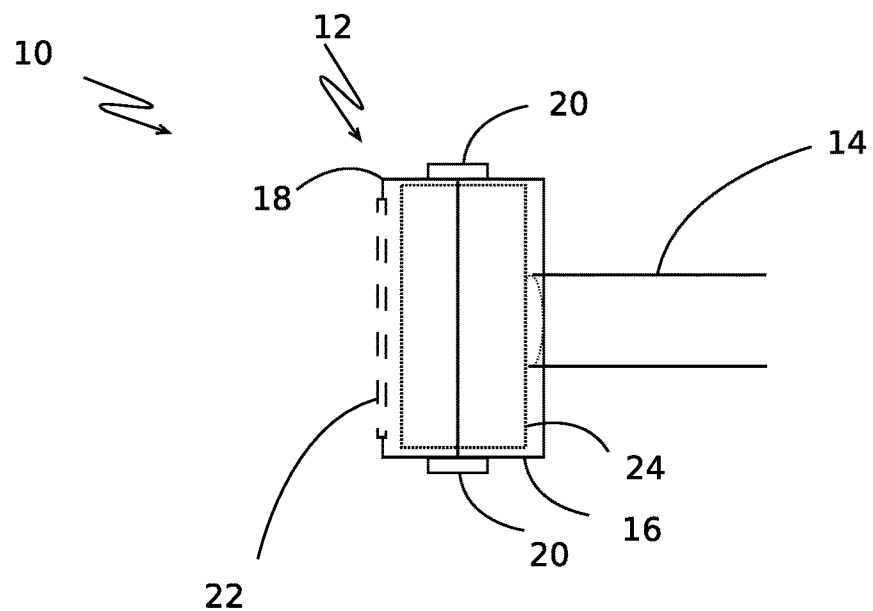
FIG. 1 is a schematic view of an extraction arm.

FIG. 1 schematically shows an extraction arm 10 with a suction head 12 which is arranged on a suction pipe 14. The suction head 12 is arranged at the open end of the suction pipe 14.

The suction head 12 has a filter housing with a main body 16 and a cover 18. The cover 18 is arranged on the main body 16 by means of holding means 20. In addition, the cover 18 has an air inlet 22 in order to guide extracted air into the interior of the filter housing.

A filter 24 is located inside the filter housing. The filter housing and in particular the main body 16 are designed to connect the filter 24 to the suction pipe 14 in an airtight manner, so that air filtered through the filter 24 reaches the interior of the suction pipe 14. The extracted air flows through the air inlet 22 into the interior of the filter housing. The air inlet 22 can advantageously guide the air flow to the filter 24.

Figure 2:
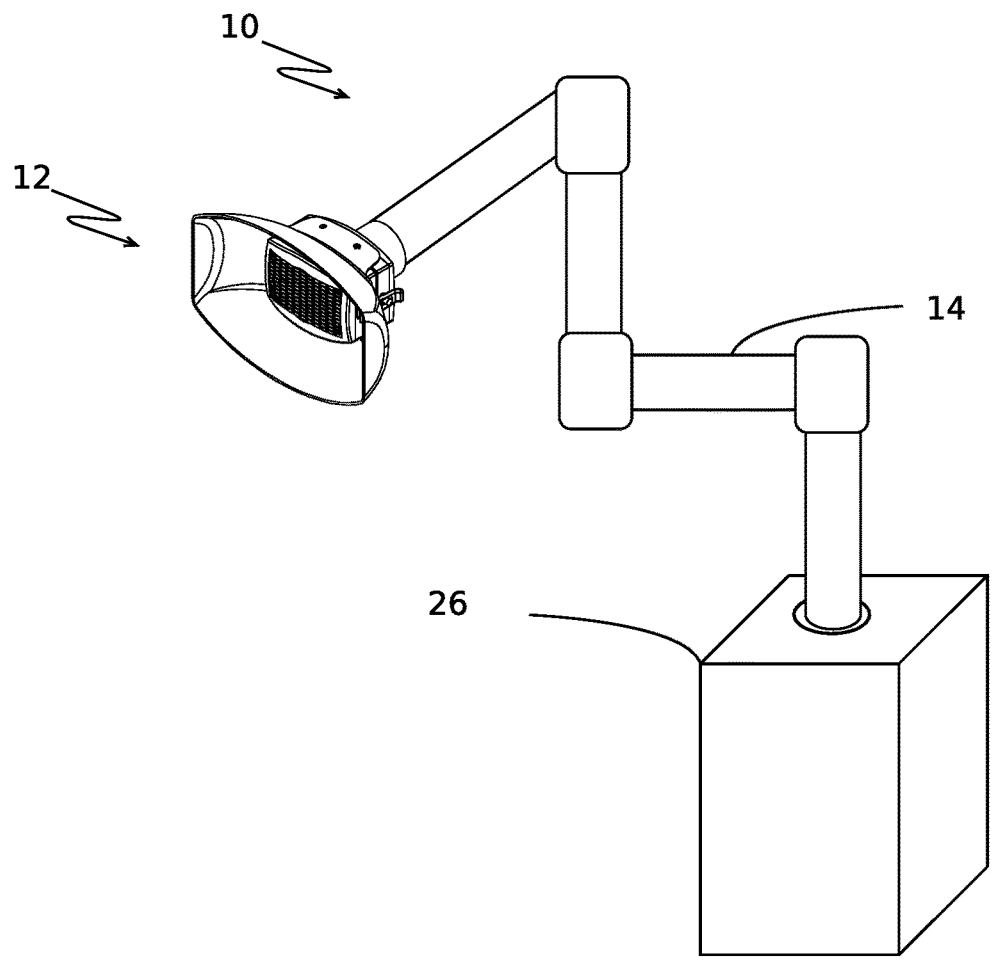
FIG. 2 is a simplified perspective view of an extraction device with the extraction arm.

FIG. 2 shows an extraction device 26 with an extraction arm 10.

The extraction arm 10 has a suction head 12 which is connected to the extraction device 26 by means of the suction pipe 14. The suction head 12 has a collecting device in the form of an extraction hood. The filter housing is arranged in the center of the collecting device. The extraction device 26 with the extraction arm 10 can be used, for example, when treating a patient in order to reliably extract dirt, pollutants, viruses and bacteria. The suction head 12 can ensure that the suction pipe 14 remains substantially clean and germ-free. The filter 24, which is arranged in the center of the suction head 12, can easily be changed after the treatment.

Figure 3:
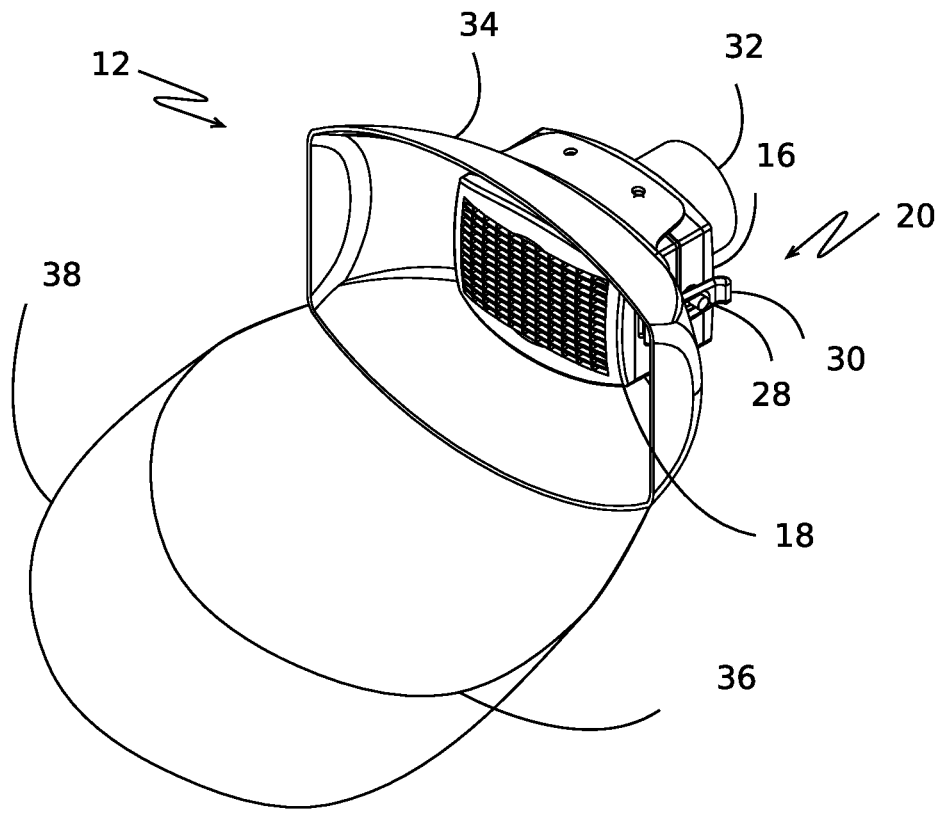
FIG. 3 shows only the suction head of the extraction arm of FIG. 2.

FIG. 3 shows the suction head 12 in more detail. In the example shown, the holding means 20 comprises a pin 28, which is arranged on the main body 16, and a latching means in the form of a spring element 30, which is designed to be resilient away from the main body 16 and forms a type of tab that can wrap around the pin 28. The pin 28 is consequently received in the tab, the spring element 30 latching in place due to the spring action and thus fixing the cover 18 on the main body 16. Advantageously, the spring element 30 is slightly inclined at the end facing away from the cover 18, so that when the cover 18 is pushed onto the main body 16, the spring element 30 is pressed outwardly by the pin 28 due to the inclination counter to the spring action and, when the cover 18 is pushed in further, springs back in the direction of the main body 16 as soon as the pin 28 reaches a recess in the spring element 30. The spring element 30 holds the cover 18 in a closed position.

The main body 16 has a connecting piece 32 for attachment to the suction pipe 14 (see FIG. 1). Here, the connecting piece 32 is designed as a round flange, so that the main body 16 can be slipped onto the suction pipe 14. It goes without saying that the connecting piece 32 can have a seal and/or an adhesive layer in order to achieve a firm and tight connection with the suction pipe 14.

The suction head 12 further comprises an extraction hood 34. The extraction hood 34 can be attached to the filter housing, for example by screwing, gluing, snapping into place and/or screwing on. The extraction region of the suction head 12 is modified by means of the extraction hood 34. A first extraction region 36 and a second extraction region 38 are shown by way of example in FIG. 3. The extraction regions 36, 38 can be defined, for example, in such a way that 99.9% of a pollutant is extracted in the first extraction region 36, whereas only 95% of the pollutant is extracted in the second extraction region 38.

It goes without saying that the extraction region depends, among other things, on an alignment of the suction head 12, the design of the collecting device, such as the extraction hood 34, and the pollutant to be extracted. In particular, an extraction region can include both an extraction surface and an extraction volume. The collecting device can alternatively also be designed as a suction nozzle.

Figure 4:
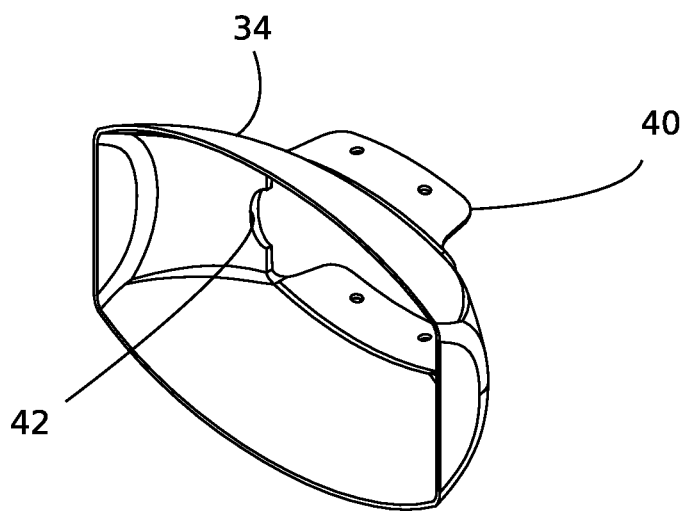
FIG. 4 shows only the extraction hood of the suction head of FIG. 3.

FIG. 4 shows the extraction hood 34 in detail. The extraction hood 34 has a connecting portion which is designed in the form of two connecting parts 40 which extend in the direction of the suction pipe. On the side facing the filter housing, the connecting part 40 preferably has a shape corresponding to the outside of the filter housing. The connecting portion 40 has two bores in order to screw the extraction hood 34 onto the filter housing. It goes without saying that the connecting part 40 can also be designed to be resilient, the connecting part 40 being able to recede outwards and to be fastened to the filter housing in a latching manner with corresponding pins.

The extraction hood 34 also has recesses 42. The recesses 42 are designed in such a way that the spring element 30 of the cover 18 can be passed through the recesses 42 and can be held by the pin 28 on the rear side of the extraction hood 34, as shown in FIG. 3.

Figure 5:
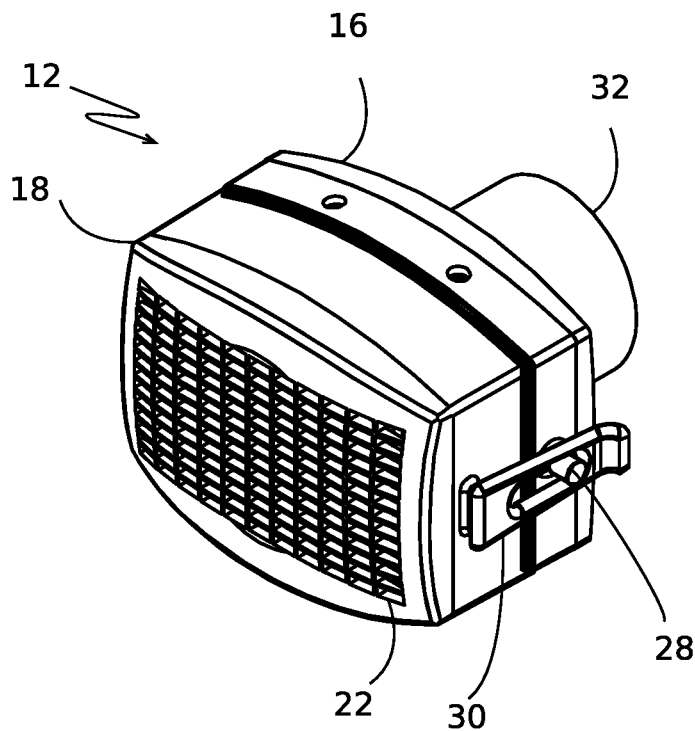
FIG. 5 shows only the filter housing of the suction head of FIG. 3, in the closed state.

In FIG. 5, the filter housing can be seen without the extraction hood 34. Like reference signs relate to like features and will not be explained again. The mode of operation of the latching means in the form of a spring element 30 can be explained in more detail with reference to FIG. 5. The spring element 30 comprises an arm or a tab which has a recess, the pin 28 being able to engage in the recess of the spring element 30. In this way, the cover 18 can be releasably but firmly attached to the main body 16. The spring element 30 can be resilient in the outward direction. For example, this can be achieved by weakening the material in the connection between the spring element 30 and the cover 18. It goes without saying that a metal connection or a spring can also be provided in order to enable the spring element 30 to recede in a resilient manner. As already described above, the spring element 30 has a curvature at the end facing the suction pipe, so that when the cover 18 is pushed on, the spring element 30 is pressed outward due to the interaction of the curvature of the spring element 30 with the pin 28. When the cover 18 is pushed in further in the direction of the suction pipe, the spring element 30 snaps inwards due to the spring action when the pin 28 penetrates the recess in the latching means 30. As a result, the cover 18 can be arranged on the main body 16 by simply being slid on from the front, i.e. from the extraction region. By bending the spring element 30 against the spring action, i.e. pulling it outward, the locking connection can be released and the cover 18 removed from the main body 16. When the extraction hood 34 is in place, the spring element 30 can be actuated behind the extraction hood 34.

The main body 16 also has two bores which are provided for connecting the main body 16 to the extraction hood 34.

Figure 6:
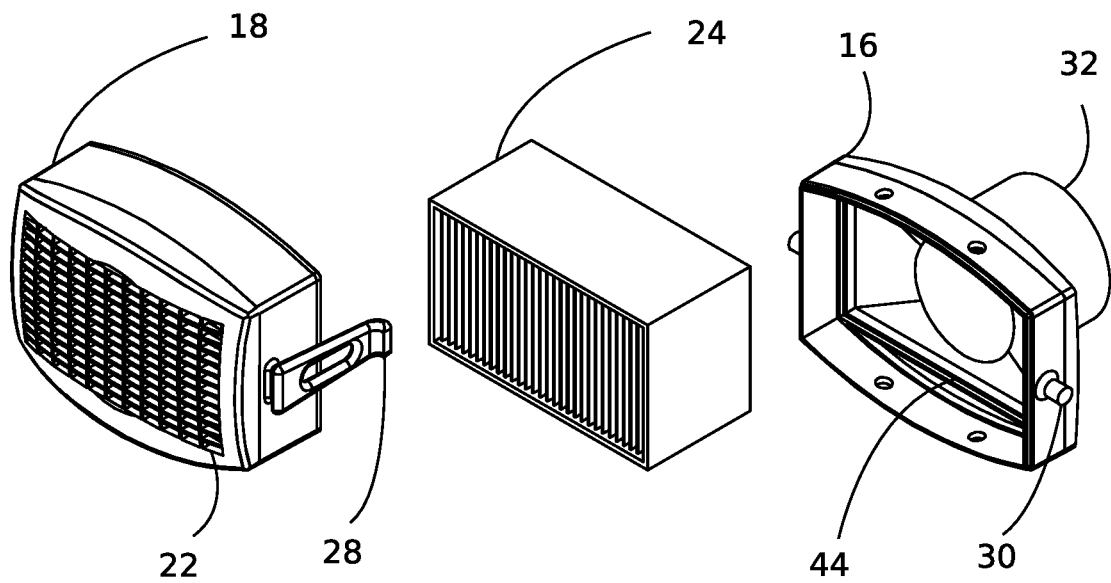
FIG. 6 shows the opened filter housing with the filter, in an exploded view.

FIG. 6 is an exploded view of the filter housing according to FIG. 5. The filter 24 is cuboid. The filter 24 can be inserted into the main body 16. The main body 16 has a placement edge 44 in order to allow the filter 24 to be securely seated in a predefined position in the filter housing. The placement edge 44 can have a seal, in particular a rubber seal, in order to allow an airtight connection of the filter 24 to the main body 16. This design makes it possible to remove the filter 24 from the filter housing and to replace it with a fresh filter quickly and without using tools.

In the claims, the words "comprise" and "having" do not preclude the presence of further elements. The indefinite article "a" or "an" does not preclude the presence of a plurality. A single element or a single unit can perform the functions of several of the units mentioned in the claims.

LIST OF REFERENCE SIGNS

10 Extraction arm
12 Suction head
14 Suction pipe
16 Main body
18 Cover
20 Holding means
22 Air inlet
24 Filter
26 Extraction device
28 Pin
30 Spring element
32 Connecting piece
34 Extraction hood
36 First extraction region
38 Second extraction region
40 Connecting part
42 Recess
44 Placement edge

The invention claimed is:

1. An extraction arm for an extraction device, comprising:
a suction pipe; and
a suction head,
wherein the extraction arm defines a suction path that extends from an extraction region in the surroundings of the suction head through the suction pipe to the extraction device,
wherein the extraction arm comprises an exchangeable filter which is arranged within the suction path,
wherein the filter is accommodated in a filter housing and the filter housing is designed to connect the filter and the suction pipe in an airtight manner,
wherein the filter housing has a main body which is connected to the suction pipe and a removable cover for closing the filter housing, and
wherein the cover of the filter housing is releasably attached to the main body by a latching means, the latching means comprising a spring element on the cover, and the spring element extends through a recess in an extraction hood in order to latch with the main body.

2. The extraction arm according to claim 1, wherein the main body has a connecting piece for connection to the suction pipe.

3. The extraction arm according to claim 1, wherein the cover has an air inlet, in order to guide extracted air into the interior of the filter housing.

4. The extraction arm according to claim 1, wherein the cover of the filter housing is accessible from the extraction region in order to replace the filter without using tools.

5. The extraction arm according to claim 4, wherein the suction head comprises the extraction hood, in the center of which the filter housing is located.

6. The extraction arm according to claim 5, wherein the extraction hood is connected to the main body.

7. A method comprising applying the extraction arm according to claim 1 with a medical extraction device.

* * * * *